United States Patent
Hauptmann et al.

(10) Patent No.: US 9,872,746 B2
(45) Date of Patent: Jan. 23, 2018

(54) TRANSLUCENCY ENHANCING SOLUTION FOR ZIRCONIA CERAMICS

(71) Applicant: 3M INNOVATIVE PROPERTIES COMPANY, Saint Paul, MN (US)

(72) Inventors: Holger Hauptmann, Sindelsdorf (DE); Andreas Herrmann, München (DE); Brant U. Kolb, Afton, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 344 days.

(21) Appl. No.: 14/418,975

(22) PCT Filed: Mar. 8, 2013

(86) PCT No.: PCT/US2013/029743
§ 371 (c)(1),
(2) Date: Feb. 2, 2015

(87) PCT Pub. No.: WO2014/021940
PCT Pub. Date: Feb. 6, 2014

(65) Prior Publication Data
US 2015/0157430 A1  Jun. 11, 2015

(30) Foreign Application Priority Data
Aug. 3, 2012 (EP) ..................... 12179130

(51) Int. Cl.
*A61C 13/08* (2006.01)
*C04B 35/486* (2006.01)
(Continued)

(52) U.S. Cl.
CPC .............. *A61C 13/082* (2013.01); *A61C 5/77* (2017.02); *A61C 7/12* (2013.01); *A61C 13/0006* (2013.01);
(Continued)

(58) Field of Classification Search
CPC .............. A61C 13/082; A61C 13/0022; A61C 2201/002; A61C 2201/005; A61C 19/10; A61K 6/0002; A61K 6/024
(Continued)

(56) References Cited

U.S. PATENT DOCUMENTS 6,709,694 B1   3/2004  Suttor
8,309,015 B2   11/2012 Rolf et al.
(Continued)

FOREIGN PATENT DOCUMENTS

CN  102344285  2/2012
EP  2573060    3/2013
(Continued)

OTHER PUBLICATIONS

Jaroniec, "Comparative studies of structural and surface properties of porous inorganic oxides used in liquid chromatography", Journal of Chromatography A, 1998, vol. 797, pp. 93-102.
(Continued)

*Primary Examiner* — Nicholas Lucchesi
*Assistant Examiner* — Shannel Wright

(57) ABSTRACT

The invention relates to kit of parts comprising a solution, a porous zirconia article, optionally application equipment, the solution comprising cation(s) of non-coloring agent(s) selected from ions of Y, Gd, La, Yb, Tm, Mg, Ca and mixtures thereof, solvent(s) for the ion(s), optionally complexing agent(s), optionally thickening agent(s), optionally organic marker substance(s), optionally additive(s), the porous zirconia article showing a N2 adsorption and/or desorption of isotherm type IV according to IUPAC classification. The invention also relates to a method for enhancing the translucency of a zirconia article comprising the steps of providing a porous zirconia article and a solution, applying the solution to at least a part of the outer surface of
(Continued)

the porous zirconia article, optionally drying the porous zirconia article of the preceding step, sintering the porous zirconia article to obtain a zirconia ceramic article.

13 Claims, 1 Drawing Sheet

(51) Int. Cl.

| | | |
|---|---|---|
| *C04B 35/624* | (2006.01) | |
| *C04B 38/00* | (2006.01) | |
| *C04B 41/85* | (2006.01) | |
| *C04B 41/00* | (2006.01) | |
| *C04B 41/50* | (2006.01) | |
| *A61C 7/12* | (2006.01) | |
| *A61C 13/01* | (2006.01) | |
| *C04B 35/48* | (2006.01) | |
| *A61C 5/77* | (2017.01) | |
| *A61C 13/00* | (2006.01) | |
| *C04B 111/00* | (2006.01) | |
| *A61C 13/083* | (2006.01) | |
| *A61C 8/00* | (2006.01) | |

(52) U.S. Cl.
CPC ............. *A61C 13/01* (2013.01); *C04B 35/48* (2013.01); *C04B 35/486* (2013.01); *C04B 35/624* (2013.01); *C04B 38/0045* (2013.01); *C04B 41/009* (2013.01); *C04B 41/501* (2013.01); *C04B 41/85* (2013.01); *A61C 8/0012* (2013.01); *A61C 13/0003* (2013.01); *A61C 13/0022* (2013.01); *A61C 13/083* (2013.01); *C04B 2111/00836* (2013.01); *C04B 2235/3225* (2013.01); *C04B 2235/3244* (2013.01); *C04B 2235/449* (2013.01); *C04B 2235/616* (2013.01); *C04B 2235/6562* (2013.01); *C04B 2235/6565* (2013.01); *C04B 2235/6567* (2013.01); *C04B 2235/661* (2013.01); *C04B 2235/9653* (2013.01); *Y10T 428/24997* (2015.04)

(58) Field of Classification Search
USPC ........................................................ 501/103
See application file for complete search history.

(56) References Cited

U.S. PATENT DOCUMENTS

| | | |
|---|---|---|
| 8,398,401 B2 | 3/2013 | Hayashi |
| 8,398,402 B2 | 3/2013 | Hayashi |
| 8,697,176 B2 | 4/2014 | Wang et al. |
| 2006/0117989 A1 | 6/2006 | Hauptmann |
| 2010/0221683 A1 | 9/2010 | Franke |
| 2015/0157430 A1 | 6/2015 | Hauptmann et al. |

FOREIGN PATENT DOCUMENTS

| | | |
|---|---|---|
| JP | 2010-514665 A | 5/2010 |
| WO | WO 2000-46168 | 8/2000 |
| WO | WO 2004-110959 | 12/2004 |
| WO | WO 2008-098157 | 8/2008 |
| WO | WO 2009-014903 | 1/2009 |
| WO | WO 2013-003990 | 1/2013 |
| WO | WO 2013-022612 | 2/2013 |
| WO | WO 2014/021940 A1 | 2/2014 |

OTHER PUBLICATIONS

Sui, "Direct Synthesis of Zirconia Aerogel Nanoarchitecture in Supercritical $CO_2$", Langmuir, 2006, vol. 22, No. 9, pp. 4390-4396.
Wang, "Investigation of a new 3Y-stabilized zirconia with an improved optical property for applications as a dental ceramic", Journal of Ceramic Processing Research, 2011, vol. 12, No. 4, pp. 473-476.
1507 Extended EP Search Report for EP12179130.5, PCT/US2013/029743, dated Nov. 20, 2012, 6pgs.
International Search Report for PCT International Application No. PCT/US2013/029743, dated Apr. 26, 2013, 4pgs.

TRANSLUCENCY ENHANCING SOLUTION FOR ZIRCONIA CERAMICS

CROSS REFERENCE TO RELATED APPLICATIONS

This application is a national stage filing under 35 U.S.C. 371 of PCT/US2013/029743, filed 8 Mar. 2013, which claims priority to European Application No. EP 12179130.5, filed 3 Aug. 2012, the disclosures of which are incorporated by reference in their entirety herein.

SUMMARY OF INVENTION

The invention is directed to a solution containing non-colouring ions. The solution can be used for enhancing the translucency of zirconia ceramics, especially the translucency of dental ceramic materials.

BACKGROUND

Natural tooth shows a complex gradient in translucency, beginning from translucent (enamel) to nearly opaque (dentin) from outer to inner area. Translucency is therefore an important property of dental materials where esthetic matters. The current way to achieve best esthetics in high loaded all ceramic restoration is veneering a high strength ceramic (e.g. Zirconia) material with a low strength high translucent and glass-based veneering ceramic. The veneering step has to be done in most cases by a skilled lab technician and is often time consuming and expensive. Due to the weakness of the veneering porcelain chipping is often observed in several clinical cases.

Another way to produce hard dental tissue saving restorations is using monolithic zirconia without veneering in areas where esthetics play only a minor role (e.g. in the posterior regions of the dental situation).

Zirconia restorations are typically produced via a CAD/CAM process:
  A restoration is milled out of a pre-sintered zirconia mill blank.
  Afterwards the esthetic of the restoration is increased by colouring the material with a coloring liquid.
  The restoration is finished by sintering and polishing.

WO 2004/110959 relates to a colouring solution for ceramic framework. The solution comprises a solvent (e.g. water), a metal salt and polyethylene glycol having a Mn in the range of 1.000 to 200.000.

WO 00/46168 A1 (corresponding to U.S. Pat. No. 6,709,694 B1) refers to colouring ceramics by way of ionic or complex-containing solutions containing defined concentrations of at least one salts or complexes of the rare earth elements or of the elements of the subgroups. The solution might contain additives like stabilizers, complex builders, pigments and beating additives.

WO 2008/098157 relates to a colouring solution for dental ceramic framework comprising a solvent, a colouring agent comprising metal ions, and a complexing agent, wherein the amount of complexing agent is sufficient to dissolve the colouring agent in the solvent.

WO 2009/014903 relates to a colouring solution for dental ceramic articles, the solution comprising a solvent and a colouring agent comprising rare earth element ions being present in the solution in an amount of at least about 0.05 mol/l solvent and transition ions being present in the solution in an amount of about 0.00001 to about 0.05 mol/l solvent.

CN 102344285 (corresponding to WO 2013/003990) relates to method how to change light transmission of dental zirconia materials. A pre-sintered Y-TZP zirconia is dipped in or brushed with an yttrium containing solution for 2 to 15 min. The zirconia is dried and sintered at 1400 to 1600° C. for 2 h.

Colouring liquids for dental ceramics are meanwhile known in the art.

Examples of colouring solutions are described in U.S. Pat. No. 6,709,694, US 2006/0117989, WO 2009/014903, EP application No. 11177189. The content of these references is herewith incorporated by reference. Theses colouring liquids typically comprise water, metal cations selected from rare earth elements, transition metal and mixtures thereof, and sometimes a complexing agent or further additives like (poly)ethylene glycol. The colouring liquids are typically used for homogeneously colouring dental ceramics and in particular porous dental ceramic framework.

The present invention is intended to improve the known colouring solutions and to extend its use.

DESCRIPTION OF INVENTION

In particular, there is a need to mimic the natural tooth appearance in dental restorations taking into account individual degrees of translucency of the hard dental tissue e.g. of enamel and dentin.

It should be possible to produce a dental restoration out of a monolithic block in an economic way if possible without significant loss of strength and durability. Moreover a smooth transition of the appearance from translucent to opaque is often desirable.

Thus, there is a desire for means to enhance the translucency of zirconia articles, especially zirconia ceramic articles.

If possible, these means should be easy to apply and comparable cheap in production.

In one aspect the invention is directed to a kit of parts comprising
  a solution,
  a porous zirconia article,
  optionally application equipment,
the solution comprising
  cation(s) of Y, Gd, La, Yb, Tm, Ca, Mg and mixtures thereof,
  solvent(s) for the non-colouring ion(s),
  optionally a complexing agent(s),
  optionally thickening agent(s),
  optionally organic marker substance(s),
  optionally additive(s),
the porous zirconia article showing a N2 adsorption and/or desorption of isotherm type IV according to IUPAC classification and/or showing a hysteresis loop when analyzed with regard to its adsorption and/or desorption behavior to nitrogen, especially a N2 adsorption and desorption of isotherm type IV and a hysteresis loop of type H1 according to IUPAC classification.

Yet another aspect of the invention is directed to a method for enhancing the translucency of a zirconia article comprising the steps of
  providing a porous zirconia article and a solution as described in the present text,
  applying the solution as described in the present text to at least a part of the outer surface of the porous zirconia article,
  optionally drying the porous zirconia article of the preceding step, sintering the porous zirconia article to obtain a zirconia ceramic article.

The invention is also directed to a (sintered) zirconia ceramic article obtainable by the method described in the present text.

In another embodiment the invention is directed to the use of the solution as described is the present text for enhancing the translucency of a zirconia article after sintering.

Definitions

"Solution" shall mean a composition containing solvent with soluble components dissolved therein. The solution is a liquid at ambient conditions.

A "solvent" is any solvent which is able to dissolve the non-colouring ions. The solvent should be sufficiently chemically stable if combined with the effect agent and/or complexing agent. That is, the solvent shall not be decomposed by the other components present in the composition.

"Soluble" means that a component (solid) can be completely dissolved within a solvent. That is, the substance is able to form individual molecules (like glucose) or ions (like sodium cations or chloride anions) when dispersed in water at 23° C. The solution process, however, might take some time, e.g. stirring the composition over a couple of hours (e.g. 10 or 20 h) might be required.

A solution can be classified as "storage stable", if it remains stable over a considerable long period of time (at least about 4 weeks to more than about 12 months under ambient conditions). A storage stable solution typically does not show any visible (visible to the human eye) precipitation of the colouring agent during storage at ambient conditions (about 23° C., about 1013 mbar) and does not show decomposition of the solution or precipitation of single or multiple components.

The term "amount sufficient to dissolve" describes the amount of an agent needed to fully dissolve a certain substance in a certain solvent so that a storage stable composition can be obtained. The time needed to dissolve a substance is not particularly limited, however, the dissolution should occur within a reasonable time (e.g. within about 10 to about 48 h) using common equipment like mechanical stirrers and heaters.

"Solid particles" shall mean a substance being a solid having a shape which can be geometrically determined. The shape can be regular or irregular. Particles can typically be analysed with respect to e.g. grain size and grain size distribution.

A "powder" means a dry, bulk solid composed of a large number of fine particles that may flow freely when shaken or tilted.

"Cations of non-colouring agent" shall mean ions which do not have a significant absorption in the spectrum visible to the human eye (e.g. from about 380 to about 780 nm), which results in a non-coloured solution, if the ions are dissolved in water (e.g. in an amount of 0.6 mol/l).

An absorption can be characterized as "significant", if the intensity of the absorption between 380 nm and 780 nm is above about 20% or above about 10%.

A solution is defined as "non-coloured", if the a* and b* values (of the L*a*b* colour space) are as follows: a* being within a range of 0±5 or 0±3; b* being within a range of 0±20 or 0±10.

A non-coloured solution does essentially not contain or is essentially free of colouring ions.

A composition is "essentially or substantially free of" a certain component, if the composition does not contain said component as an essential feature. Thus, said component is not willfully added to the composition either as such or in combination with other components or ingredient of other components. A composition being essentially free of a certain component usually contains the component in an amount of less than about 2 wt.-% or less than about 1 wt.-% or less than about 0.1 wt.-% or less than about 0.01 wt.-% (or less than about 0.35 mol/l solvent or less than about 0.18 mol/l solvent or less than about 0.02 mol/l solvent) with respect to the whole composition or material. The composition may not contain the said component at all. However, sometimes the presence of a small amount of the said component is not avoidable e.g. due to impurities.

"Colouring ions" shall mean ions which have an absorption in the spectrum visible to the human eye (e.g. from about 380 to about 780 nm), which results in a coloured solution (visible to the human eye), if the colouring ions are dissolved in water (e.g. 0.6 mol/l).

A solution can be characterized as "transparent" within the meaning of the invention if a beam of visible light (about 380 to about 780 nm) is not scattered by the solution and cannot be observed by side view (no Tyndall effect). However, the intensity of the penetrating beam of visible light in direction of the beam may be weakened due to absorption of the light by the colouring metal ions "Zirconia article" shall mean a 3-dimensional article wherein at least one the x, y, z dimension is at least about 5 mm, the article being comprised of at least about 80 wt.-% zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures include tetragonal, monocline, cubic zirconia and mixtures thereof.

The term "dental article" means any article which can or is to be used in the dental or orthodontic field, especially for producing of or as dental restoration, a tooth model and parts thereof.

Examples of dental articles include crowns (including monolithic crowns), bridges, inlays, onlays, veneers, facings, copings, crown and bridged framework, implants, abutments, orthodontic appliances (e.g. brackets, buccal tubes, cleats and buttons) and parts thereof.

The surface of a tooth is considered not to be a dental article.

A dental article should not contain components which are detrimental to the patient's health and thus free of hazardous and toxic components being able to migrate out of the dental article.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample.

The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

An article is classified as "absorbent" if the article is able to absorb a certain amount of a liquid, comparable to a sponge. The amount of liquid which can be absorbed depends e.g. on the chemical nature of the article, the viscosity of the solvent, the porosity and pore volume of the article. E.g. a pre-sintered ceramic article, that is an article which has not been sintered to full density, is able to absorb a certain amount of liquid. Absorbing of liquids is typically only possible if the article has an open-porous structure.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

Typical values for an "open-celled" material are between about 15% and about 75% or between about 18% and about 75%, or between about 30% and about 70%, or between about 34% and about 67%, or between about 40% to about 68%, or between about 42% and about 67%.

The term "closed-celled" relates to a "closed porosity". Closed cells are those cells which are not accessible from the outside and cannot be infiltrated by gases under ambient conditions.

The "average connected pore diameter" means the average size of the open-celled pores of a material. The average connected pore diameter can be calculated as described in the Examples section.

The term "calcining" refers to a process of heating solid material to drive off at least 90 percent by weight of volatile chemically bond components (e.g., organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. Sintering typically includes the densification of a porous material to a less porous material (or a material having less cells) having a higher density, in some cases sintering may also include changes of the material phase composition (for example, a partial conversion of an amorphous phase toward a crystalline phase).

"Diafiltration" is a technique that uses ultrafiltration membranes to completely remove, replace, or lower the concentration of salts or solvents from solutions containing organic molecules. The process selectively utilizes permeable (porous) membrane filters to separate the components of solutions and suspensions based on their molecular size.

The term "aerogel" shall mean a three-dimensional low density (i.e., less than 20% of theoretical density) solid. An aerogel is a porous material derived from a gel, in which the liquid component of the gel has been replaced with a gas. The solvent removal is often done under supercritical conditions. During this process the network does not substantially shrink and a highly porous, low-density material can be obtained.

By "machining" is meant milling, grinding, cutting, carving, or shaping a material by a machine. Milling is usually faster and more cost effective than grinding. A "machinable article" is an article having a 3-dimensional shape and having sufficient strength to be machined.

"Isotropic sintering behaviour" means that the sintering of a porous body during the sintering process occurs essentially invariant with respect to the directions x, y and z. "Essentially invariant" means that the difference in sintering behaviour with respect to the directions x, y and z is in a range of not more than about +/−5% or +/−2% or +/−1%.

"Ambient conditions" mean the conditions which the inventive solution is usually subjected to during storage and handling. Ambient conditions may, for example, be a pressure of about 900 to about 1100 mbar, a temperature of about 10 to about 40° C. and a relative humidity of about 10 to about 100%. In the laboratory ambient conditions are adjusted to about 20 to about 25° C. and about 1000 to about 1025 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Figure 1:
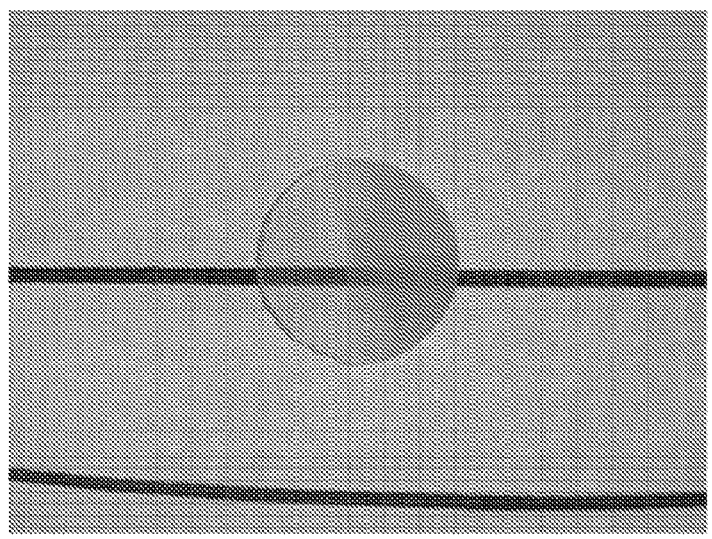
FIG. 1 shows a zirconia ceramic disc, a section of which has been treated with the solution described in the present text.

It has been found that the solution described in the present text is suitable for enhancing the translucency of a zirconia ceramic after sintering.

The solution typically has a sufficient viscosity not only to be applied to parts of the surface of a zirconia article but also to migrate into the pores of a porous zirconia article.

Without wishing to be bound to a certain theory it is believed that the non-colouring ions contained in the solutions are incorporated into the zirconia material during sintering and influence the crystalline structure.

It was found that the translucency of the zirconia article can be improved by enhancing the content of the cubic crystalline phase of the zirconia article.

In order to enhance the cubic crystalline phase content of a zirconia ceramic, a sufficient amount of suitable ions has to be incorporated.

The solution described in the present text is especially suitable for producing highly aesthetic dental ceramic articles, in particular dental ceramic articles like crowns where only a part of the outer surface of the dental article has been treated with the solution.

Such a procedure facilitates the production of individualized dental ceramic articles imitating the natural appearance of a tooth having a rather opaque core (dentin) and a rather translucent shell (enamel).

In particular, the solution and process described in the present text enable the practitioner to provide highly esthetic monolithic dental restorations.

It has been found that the inventive solution is in particular useful for enhancing the translucency of zirconia articles having been obtained when sintering porous zirconia articles having properties as described in the text below. Especially suitable are porous zirconia articles obtained when heat-treating a zirconia aerogel block.

With this invention it is now possible to individualize dental restorations not only by color but also by translucency.

The invention relates to a kit of parts for producing a dental ceramic article comprising
  a solution,
  a porous zirconia article, and
  optionally application equipment,
the solution comprising
  cation(s) of non-colouring agent(s) selected from ions of Y, Gd, La, Yb, Tm and mixtures thereof,
  solvent(s) for the ion(s),
  optionally complexing agent(s),
  optionally thickening agent(s),
  optionally organic marker substance(s),
  optionally additive(s),
the porous zirconia article showing a N2 adsorption and/or desorption of isotherm type IV according to IUPAC classification.

The solution and the porous zirconia article described in the present text are in particular useful for producing a dental ceramic article out of a monolithic block. Producing a dental ceramic article out of a monolithic block has to address the discrepancy between sufficient strength on the one hand and desired translucency on the other hand.

This discrepancy can be addressed as follows:
  The porous zirconia material should have a sufficient strength, so that it can be machined. This can be achieved by providing a pre-sintered material.
  The load bearing part of the dental article should be sufficiently strong. This can be achieved by providing a zirconia material which has a tetragonal stabilized phase (after sintering).
  The zirconia material to be treated with the solution should have a sufficient open porosity. This will facilitate the up-take of the solution.
  In order to increase the translucency, the solution should not contain a high amount of colouring ions.
  If desired, the solution might contain organic additives to support penetration of the solution into the pores of the zirconia material to be treated.
  If desired, the solution might contain organic thickening additives to control depth of penetration and spreading of the solution.
  If desired, the solution might contain in addition ionic additives being able to color the dental restoration.
  If desired, the solution might contain organic additives to mark the treated areas.

Thus, the present invention also facilitates the production of a dental ceramic article out of a monolithic block of zirconia material, the dental ceramic article (after sintering) having an area (e.g. framework) containing a comparable high content of tetragonal phase containing zirconia material and an area (e.g. surface region) containing a comparable high content of cubic phase containing zirconia material.

According to a one embodiment, the solution is characterized by at least one of the following parameters:
  pH value: from about 0 to about 9 or from about 1 to about 7 or from about 2 to about 6;
  viscosity: from about 1 to about 10,000 mPa*s or from about 100 to about 6,000 mPa*s or from about 500 to about 3,000 mPa*s (measured at 23° C.);
  essentially no or no significant light absorption in the range from: about 380 to about 780 nm;
  showing a transmission contrast ratio (CT-R) above about 80 or above about 82 or above about 85 or above about 90%;
  being non-coloured.

If desired, the pH-value, the viscosity, light absorption and transmission contrast ratio can be determined as described in the Example section below.

If the solution is a water containing (aqueous) solution, it typically has a pH value in the range of 0 to 9, that is from strong acidic to slightly basic.

If the pH value of the solution is outside this range, it might be difficult to achieve a storage stable solution. In particular, the cations of the non-colouring agent might start to precipitate from the solution.

If the solution does not contain a complexing agent, a pH value in the acidic range is typically preferred. If the solution, however, contains a complexing agent, the pH value may be in a range from slightly acidic to slightly basic (e.g. 3 to 9 or 4 to 8).

The solution has typically an adequate viscosity so that a sufficient amount of solution can not only be applied to the surface of the zirconia article but also is able to migrate into the pores of the zirconia article.

Adjusting the viscosity to a value as indicated above can be beneficial in that the solution can be more accurately applied to particular sections or regions of the porous zirconia article.

If the viscosity of the colouring solution is too high, the solution might not be able to sufficiently enter the pores of the zirconia material. On the other hand, if the viscosity of the solution is too low, the solution might migrate into the pores too rapidly and might diffuse into the whole article.

In a further embodiment the solution is transparent.

As the solution described in the present text is intended to be used for enhancing the translucency of a zirconia ceramic, the solution as such should also be essentially translucent. Otherwise, it might be difficult to obtain the intended result.

In a further embodiment, the solution containing the solvent and the non-coloring ions does essentially show no absorption in the range from: about 380 to about 780 nm. That means the solution is essentially color-less to the human eye.

A high absorption in the regions specified above could result in an undesired colored zirconia article after sintering.

The solution comprises cations of non-colouring agent(s).

The cations are selected from ions of Y, Gd, La, Yb, Tm, Ca, Mg and mixtures thereof.

The solution may contain only one of the above cations or a combination of the above cations.

A solution containing cations of Y is sometimes preferred. However, it is also possible to use combinations of ions including Y and La or Y and Yb or Y and Gd or Y and Tm.

The non-coloring agent is typically added as a salt comprising cations and anions.

The anions are typically selected from the group consisting of $NO_3^-$, $NO_2^-$, $CO_3^{2-}$, $HCO_3^-$, $ONC^-$, halogen anions (fluoride, chloride, bromide), acetates and mixtures thereof.

The cations are typically present in an amount of about 0.3 to about 5 mol/l or about 0.4 to about 4 mol/l or about 0.5 to about 3 mol/l or about 0.6 to about 2 mol/l The solution also comprises a solvent for the non-coloring ion(s). If desired, mixtures of different solvents can be used.

Suitable solvents include water, alcohols (especially low-boiling alcohols, e.g. with a boiling point below about 100° C.) and ketons.

The solvent should be able to dissolve the non-coloring ions used.

Specific examples of solvents which can be used for dissolving the cations of the non-colouring agent include water, methanol, ethanol, iso-propanol, n-propanol, butanol, aceton and mixtures thereof.

Typically, the complexing agent is present in the solution in an amount sufficient to dissolve at least the cations of the non-coloring agent in the solvent or to prevent precipitation of these cations.

The solvent is typically present in an amount sufficient to dissolve the components contained or added to the solvent.

The solvent is typically present in an amount from about 20 to about 98 wt.-% or from about 30 to about 90 wt.-% or from about 35 to about 85 wt.-%, wt.-% with respect to the whole solution.

The solution may also contain on or more complexing agent(s).

Adding a complexing agent can be beneficial to improve the storage stability of the solution, accelerate the dissolving process of salts added to the solution and/or increase the amount of salts which can be dissolved in the solution.

The complexing agent is typically able to form a complex with the metal ions being present in the solution. The complex formed should be soluble in the solvent. Typically the complex formed is better soluble in the solvent than in water.

E.g., the complexing agent can be used in an at least stoichiometric ratio with respect to the molar amount of the non-colouring ions contained in the solution.

Good results can be achieved, if the molar ratio of the complexing agent to the cations of the non-coloring agent is equal to or greater than about 1 or about 2 or about 3.

If the amount of complexing agent used is too low, the non-colouring agent might not be dissolved entirely.

If the amount of complexing agent used is too high, the excess complexing agent itself might remain unsolved.

The complexing agent is usually added as a separate component of the solution.

However, it can also be added or be present in form of an anion of the non-coloring agent.

Examples include acetylacetonate, crown ethers, cryptands, ethylenediaminetriacetate and its salts, ethylene diamine tetraacetate and its salts, nitrilotriacetate and its salts, citric acid and its salts, triethylentetramine, porphin, poly acrylate, poly asparagate, acidic peptides, phthalocyanin, salicylate, glycinate, lactate, propylendiamine, ascorbate, oxalic acid and its salts and mixtures thereof.

Complexing agents having anionic groups as complexing ligands can be preferred. At least parts of the complexing ligands should be anionic. Complexing agents having only uncharged complexing ligands (or even cationic ligands) like pure amines (e.g. ethylendiamin at pH values at 8 to 14) might not yield sufficiently stable solutions.

Typically, the complexing agent is present in the solution in an amount sufficient to dissolve at least the cations of the non-coloring agent in the solvent or to prevent precipitation of these cations.

The complexing agent can be present in an amount of at least about 1 wt.-% or at least about 5 wt.-% or at least about 10 wt.-% with respect to the amount of the whole composition. There is no specific upper limit, however, usually the amount of complexing agent used does not exceed an amount of about 50 wt.-% or about 40 wt.-% or about 30 wt.-% with respect to the amount of the whole solution.

The solution may also contain one or more thickening agent(s).

Typically, the thickening agent(s) can be characterized by at least one of the following features:
  viscosity: from about 1 to about 2,000 mPa*s or from about 100 to about 1,500 mPa*s (measured at 23° C. at a shear rate of 50 s−1);
  free of polymerizable groups like (meth)acrylate groups, epoxy groups, carbon-carbon unsaturated groups;
  not containing elements like S, P.

Thickening agent(s) which can be used include polyol(s) (including polyvinyl alcohol), glycol ether(s) (e.g. PEG 200, PEG 400, PEG 600, diethylene glycol methyl ether, diethylene glycol ethyl ether), di- and polyalcohol(s) (including 1,2-propanediol, 1,3-propanediol, glycerol), glycerol ether, polysaccharide(s), xanthan gum, methyl cellulose and mixtures thereof.

Polyethylene glycols which can be used can be represented by formula (1)

$$R1O\text{---}(CH2\text{-}CH2\text{-}O)m\text{-}R1 \tag{1}$$

with R1=H, Acyl, Alkyl, Aryl, Alkylaryl, Polypropylglycol, Poly-THF, preferably H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, Poly-THF and
m=about 2 to about 100, preferably about 2 to about 20, more preferably about 2 to about 5

The average molecular weight (Mw) of the polyethylene glycol should be in the range of about 100 to about 5,000, preferably in the range of about 100 to about 1,000, more preferably in the range of about 100 to about 300.

If present, the thickening agent is typically present in the following amount: from about 0.01 to about 10 wt.-% or from about 0.1 to about 8 wt.-% or from about 0.2 to about 5 wt.-%, wt.-% with respect to the whole solution.

The solution may also contain marker substance(s).

Adding a marker substance(s) can be beneficial in order to enhance the visibility of the solution during use, especially, if the solution is transparent. Thus, the practitioner can easily determine to which parts of the surface of the zirconia article the solution has already been applied and which parts have not been treated yet and should remain untreated. On the other hand, if the marker substance is an organic substance, the marker substance(s) will be burnt during a later sintering step and thus not be incorporated into the crystal structure of the zirconia article.

Examples of marker substance(s) which can be used include food colorants like Riboflavin (E101), Ponceau 4R (E124), Green S (E142).

If present, the marker substance is typically present in the following amount: from about 0.01 to about 10 wt.-% or from about 0.1 to about 5 wt.-% or from about 0.2 to about 3 wt.-%, wt.-% with respect to the whole solution.

The inventive solution may also contain one or more additive(s).

Additives which can be added to the solution include stabilizers (such as methoxy phenol hydrochinone, Topanol A, and mixtures thereof), buffers (such as acetate or amino buffers and mixtures thereof), preservative agents (such as sorbic acid or benzoic acid and mixtures thereof) and mixtures thereof.

There is no need for additive(s) to be present, however, if they are present, they are typically present in an amount which is not detrimental to the purpose to be achieved when applying the solution.

If additive(s) are present, they are typically present in an amount of about 0.01 to about 10 wt.-% or from about 0.05 to about 5 wt.-% or from about 0.1 to about 3 wt.-% with respect to the whole solution.

According to one embodiment, the solution does typically not comprise at least one of the following components:
- colouring ions selected from ions of Fe, Mn, Er, Pr, V, Cr, Co, Mo and mixtures thereof in an amount above about 0.1 mol or above about 0.05 mol or above about 0.01 mol per l solvent or above about 2 or above about 1.5 or above about 1 or above about 0.5 or above about 0.2 or above about 0.1 wt.-% ions,
- solid particles settling from the solution upon storage for more than about 2 hours.

In one embodiment the solution is essentially free of colouring ions.

The solution does typically also not comprise solid particles which may or will remain on the surface of a zirconia article once the solution is applied to the surface of the zirconia article.

Thus, the solution described in the present text is neither a dispersion of solid particles in a solvent nor a slurry.

Commercially available colouring liquids may have a concentration of colouring ions up to about 0.4 mol per l solvent.

According to another embodiment, the solution comprises the components in the following amount(s):
- amount of cations of non-colouring agent(s): about 0.5 to about 30 wt.-% or about 1 to about 25 wt.-% or about 2 to about 20 wt.-% or about 3 to about 15 wt.-% or about 0.3 to about 5 mol/l or about 0.4 to about 4 mol/l or about 0.5 to about 3 mol/l or from about 0.6 to about 2 mol/l
- amount of solvent: about 20 to about 98 wt.-% or about 70 to about 95 wt.-%,
- amount of optional complexing agent(s): about 0 to about 10 wt.-% or about 0.05 to about 5 wt.-%,
- amount of optional thickening agent(s): about 0 to about 10 wt.-% or about 0.05 to about 5 wt.-%,
- amount of optional organic marker substance(s): about 0 to about 10 wt.-% or about 0.05 to about 5 wt.-%,
- optionally additive(s) in an amount of about 0 to about 10 wt.-% or from about 0.05 to about 5 wt.-%, wt.-% with respect to the whole composition.

According to another embodiment, the solution comprises:
- cation(s) selected from Y, Gd, La, Yb, Tm, Mg, Ca and mixtures thereof in an amount from about 0.5 to about 20 wt.-%, especially Y,
- cations(s) selected from Tb, Er, Mn in an amount from about 0.01 to about 1.5 wt.-%, especially Tb,
- optionally complexing agent,
- water as solvent, wt.-% with respect to the weight of the solution.

The solution can be produced by mixing its components. This can be done at room temperature or by applying heat and/or while stirring.

Applying heat and/or stirring can be beneficial in order to accelerate the dissolution process of the non-colouring ions into the solvent.

The composition is typically stirred until the cations of the non-colouring agent are completely dissolved in the solvent.

If desired, additives (like those mentioned above) can be added.

Undesired precipitations can be removed by filtering.

According to one embodiment the porous zirconia article to be treated with the solution described in the present text can be characterized by at least one of the following features:
(a) showing a $N_2$ adsorption and/or desorption of isotherm type IV according to IUPAC classification;
(b) showing a $N_2$ adsorption and desorption isotherm with a hysteresis loop,
(c) showing a $N_2$ adsorption and/or desorption isotherm of isotherm type IV according to IUPAC classification and a hysteresis loop,
(d) showing a $N_2$ adsorption and desorption isotherm of type IV with a hysteresis loop of type H1 according to IUPAC classification,
(e) showing a $N_2$ adsorption and desorption isotherm of type IV with a hysteresis loop of type H1 according to IUPAC classification in a $p/p_0$ range of 0.70 to 0.95;
(f) average connected pore diameter: from about 10 to about 100 nm or from about 10 to about 70 nm or from about 10 to about or from about 10 to about 50 nm or from about 15 to about 40;
(g) average grain size: less than about 100 nm or less than about 80 nm or less than about 60 nm or from about 10 to about 100 or from about 15 to about 60 nm;
(h) BET surface: from about 10 to about 200 $m^2/g$ or from about 15 to about 100 $m^2/g$ or from about 16 to about 60 $m^2/g$;
(i) Biaxial flexural strength: from about 10 to about 40 or from about 15 to about 30 MPa;
(j) x, y, z dimension: at least about 5 mm or at least about 10 or at least about 20 mm;
(k) Vickers hardness: from about 25 to about 150 or from about 40 to about 150 (HV 1).

A combination of the following features was found to be particularly beneficial: (a) and (h), or (a) and (b) and (h), or (b) and (c), or (c), (e), (g) and (h).

Surprisingly it was found that material showing a $N_2$ adsorption and/or desorption isotherm of isotherm type IV (according to IUPAC classification) and/or a hysteresis loop (especially in a $p/p_0$ range of 0.70 to 0.95) are particularly suitable.

The increase of translucency which can be achieved if those materials are used in combination with the solution described in the present text is far better than the increase of translucency which can be observed if commercially available so-called Y-TZP ceramic materials are used.

Commercially available Y-TZP ceramic materials typically show a $N_2$ adsorption of isotherm type II (according IUPAC classification), which was found to be less effective if the translucency should be enhanced.

Materials showing a type II isotherm are said to be macro-porous, whereas materials showing a type IV isotherm are said to be meso-porous.

In contrast to the porous zirconia article described in the present text, zirconia materials described in the prior art do neither show a $N_2$ adsorption and desorption isotherm with a hysteresis loop nor a $N_2$ adsorption of isotherm type IV (according to IUPAC classification).

Without wishing to be bound to a particular theory it is assumed that the condensation mode related to a material of isotherm type IV and a hysteresis loop type H1 may contribute to a more homogeneous infiltration of the solution into the pores of the material.

The BET surface S of zirconia materials described in the prior art is typically within a range from 2 to 9 m$^2$/g.

Thus, the porous zirconia article described in the present text has a unique combination of features, which facilitates the production of highly aesthetic ceramic articles, especially with respect to translucency.

The average grain size of the zirconia particles in the porous zirconia article described in the present text is small compared to the average grain size of the material of commercially available mill blanks.

A small grain size can be beneficial in that it typically leads to a more homogeneous material (from a chemical perspective), which may also result in more homogeneous physical properties.

Useful ranges for the x, y and z dimensions include from about 5 to about 300 or from about 10 to about 200 mm.

The porous zirconia article has a dimension suitable to be machined by with a machining device.

Further, the porous zirconia article has a flexural strength and/or a Vickers hardness suitable to machine the article by grinding or milling tools.

The average connected pore diameter of the material of the porous zirconia article is low compared to the pore diameter of the material of commercially available mill blanks (having typically an average connected pore size above about 200 nm.

An average connected pore diameter in this range can be beneficial in that it facilitates a quite homogeneous distribution of the inventive solution into the pores of the zirconia article.

A small pore diameter typically also results in a comparably huge internal surface and/or a comparably high surface energy. A huge internal surface may enhance the sorption properties of the article.

A huge internal surface, however, often requires an adjustment of the composition and physical properties of the solution to be used for treating the porous zirconia article.

If desired the above features can be determined as described in the Example section.

According to one embodiment, the porous zirconia article can be characterized by at least one of the following features:
 ZrO2 content: from about 70 to about 98 mol % or from about 80 to about 97 mol %;
 HfO2 content: from about 0 to about 2 mol % or from about 0.1 to about 1.8 mol %;
 Y2O3 content: from about 1 to about 15 mol % or from about 1.5 to about 10 mol % or from about 2 to about 5 mol %;
 Al2O3 content: from about 0 to about 1 mol % or from about 0.005 to about 0.5 mol % or from about 0.01 to about 0.1 mol %.

According to a further embodiment, the porous zirconia article has a composition being characterized by the following features:
 ZrO2 content: from about 90 to about 98 mol %,
 HfO2 content: from about 0 to about 2 mol %,
 Y2O3 content: from about 1 to about 5 mol %,
 Al2O3 content: from about 0 to about 0.1 mol %.

It was found that a higher Y$_2$O$_3$ content typically leads to an increase of the cubic crystal phase in the zirconia ceramic material after having sintered the material to final density. A higher content of the cubic crystal phase may contribute to a better translucency.

According to a particular embodiment the porous zirconia article can be characterized by the following features:
 showing a N$_2$ adsorption and/or desorption of isotherm type IV according to IUPAC classification,
 showing a N$_2$ adsorption and desorption isotherm with a hysteresis loop in a p/p$_0$ range of 0.70 to 0.95,
 average connected pore diameter: from about 15 to about 60,
 average grain size: less than about 100 nm,
 BET surface: from about 15 to about 100 m$^2$/g or from about 16 to about 60 m$^2$/g,
 Biaxial flexural strength: from about 10 to about 40 MPa,
 x, y, z dimension: at least about 5 mm,
 Vickers hardness: from about 25 to about 150,
 Density: from about 40% to about 60% of theoretical density.

According to another embodiment, the porous zirconia article can be obtained by a process comprising the step of heat treating a zirconia aerogel.

The zirconia aerogel can typically be characterized by at least one of the following features:
a. comprising crystalline zirconia particles having an average primary particle size in a range from 2 nm to 50 nm or from about 2 nm to about 30 nm or from about 2 to about 20 or from about 2 to about 15 nm;
b. content of crystalline zirconia particles: at least about 85 mol.-%;
c. having an organic content of at least 3 wt.-% or within a range from about 3 to about 10 wt.-%;
d. x, y, z dimension: at least about 5 or at least about 8 or at least about 10 or at least about 20 mm.

A combination of the features (a) and (b) or (a) and (c) or (a), (b) and (c) can be preferred.

The heat treatment for obtaining the porous zirconia article is typically done under the following conditions:
 temperature: from about 900 to about 1100° C. or from about 950 to about 1090° C.; from about 1000 to about 1080° C.;
 atmosphere: air or inert gas (e.g. nitrogen, argon);
 duration: until a density of about 40 to about 60 of the final density of the material has been reached.

The heat treatment can be conducted in one or more steps.

In a first heat treatment step a binder burn-out could be performed to remove all organic additives from previous process steps to obtain a so called "white body".

In a second heat treatment step the strength and/or the hardness of the white-body could be adjusted to the needs of the follow up processes like machining. In case of a machinable blanks the sintering protocol should reflecting the interaction of temperature with strength and/or hardness.

If the temperature is too low, the hardness and/or strength of the resulting article might be too low. This can cause problems during a later machining step, e.g. with respect to chipping.

If, on the other hand, the temperature is too high, the hardness and/or strength of the material may become too high. This can cause problems during a later machining step as well, e.g. with respect to the machining tool durability.

The dwell time (that is the time during which the aerogel is kept at that temperature) is not very critical. The dwell time can be zero. The dwell time, however, can also be in a range from about 0 to about 24 h or from about 0.1 to about 5 h.

If the dwell time is too long, the dental milling blocks may become too hard to be machined under reasonable conditions.

According to one embodiment, the porous zirconia article can be obtained by a process comprising the steps of
- providing a zirconia sol comprising crystalline metal oxide particles and a solvent,
- optionally concentrating the zirconia sol to provide a concentrated zirconia sol,
- mixing the sol with a polymerizable organic matrix (e.g. adding a reactive surface modifier to the zirconia sol and optionally an initiator being able to polymerizable surface-modified particles of the zirconia sol);
- optionally casting the zirconia sol into a mould to provide a casted zirconia sol,
- curing the polymerizable organic matrix of the zirconia sol to form a gel (sometimes also referred to as gelation step),
- removing the solvent from the gel (e.g. by first removing water, if present, from the gel via a solvent exchange process to provide an at least partially de-watered gel; followed by a further extraction step where the remaining solvent is extracted e.g. via super critical extraction) to provide the aerogel,
- optionally cutting the aerogel into smaller pieces,
- heat-treating the aerogel to obtain e.g. a machinable material or article.

Examples of application equipment which can be included in the kit of parts described in the present text include brushes, sponges, (hollow) needles, pens, and mixing appliances.

Examples of mixing appliances include mixing wells, trays, plates and slides.

According to one embodiment the solution is applied to the surface of the zirconia article with a pen, the pen comprising a housing, a brush tip, a removable cap and a reservoir for storing the non-water based solution described in the present text.

The brush tip is typically attached or fixed to the front end of the housing. The reservoir is typically fixed or attached to the rear end of the housing. The removable cap is typically used for protecting the brush tip during storage.

Using a pen may facilitate the application of the solution and will help the practitioner to save time.

Currently, colouring solutions are usually offered in bottles and are applied to porous ceramics with a separate brush or even by dipping the entire ceramic into the colouring solution. This often goes along with a lot of waste of the colouring solution. By using a pen, there will be essentially no waste of the colouring solution.

Further, a pen with a cap will prevent the pen from drying out if not used.

Providing individual pens for individual colouring solutions may further facilitate the application of the composition to the surface of porous dental ceramic(s). Until now, usually only one brush is used and that brush has to be cleaned thoroughly before a further colouring solution is applied.

If, however, one pen for one colour is provided, switching the colours during the application process is quite easy and more save for the dental technician, while mixing of different colours using this kind of equipment is still possible by subsequent application of different colours to the ceramic surface.

The volume of the reservoir may be in a range from about 1 ml to about 10 ml or from about 2 ml to about 5 ml.

The reservoir may be removable or fixed to the housing of the pen.

According to one embodiment, the reservoir is exchangeable. The exchangeable reservoir may have the shape of a cartridge or bullet.

The brush tip typically comprises bristles. The material the bristles are made of can be selected from artificial or natural materials. Artificial materials include polyamides (nylon), polyesters and mixtures thereof. Natural materials usually include different kinds of animal hair. The brush tip may be removable or exchangeable, too.

The length of the brush tip extending from the pen is typically within a range from about 5 to about 20 mm or from about 8 to about 15 mm. If the bristles are too short, application of the solution to the inside of a dental restoration may be difficult. If, on the other hand, the bristles are too long, the handling of the brush itself might become impractical for dental applications.

The thickness of the brush tip at its base is typically in the range from about 0.3 to about 5 mm or from about 1 to about 4 mm. If the tip is too broad, application of the solution to the inside of a dental restoration may be difficult. If, on the other hand, the tip is too narrow, the handling of the brush itself might become impractical for dental applications.

Furthermore, if the length and the thickness of the brush tip is either too low or too high, it will be difficult to apply the solution properly, that is either too little to too much of the solution is applied. Both may be detrimental for achieving an accurately coloured dental ceramic.

The shape of the brush tip should be tapered and fan out, if desired, when pressure is applied. Thus, the brush tip should have some flexibility. A brush tip with these properties can be used to draw thin lines and also to paint on larger areas.

A combination of a brush tip comprising bristles having a length from about 8 to about 15 mm with the solution described in the present text having a viscosity above about 200 mPa*s or above about 500 mPa*s (measured at 23° C.) was found to be beneficial. Such a combination facilitates the accurate application of the solution on the surface of the porous dental ceramic(s).

Thus, the invention is also directed to a pen as described in the present text comprising the solution.

The solution is typically used for being selectively applied to parts of the surface of a zirconia article, in particular to a dental article. That is, the solution is only applied to parts of the surface of the article but usually not to the whole surface. In contrast to commercially available colouring liquids, the article is not dipped completely into the inventive solution.

Moreover, the solution cannot only be applied to dry surfaces of zirconia articles, but also to wetted surfaces, especially to pre-sintered zirconia dental articles.

The invention is also directed to a method for enhancing the translucency of a zirconia article, the method comprising the steps of
- providing a porous zirconia article as described in the present text and a solution as described in the present text,
- applying the solution to at least a part of the outer surface of the porous zirconia article,
- optionally drying the porous zirconia article of the preceding step,
- sintering the porous zirconia article to obtain a zirconia ceramic article.

The porous zirconia article is typically in a pre-sintered stage. Such an article has usually open pores and thus can be described as absorbent.

Selectively applying the solution to the surface of the porous zirconia article is usually achieved by painting e.g. using a brush. However, the solution can also be applied by using a sponge, a fabric, brush-pen or by spraying, equipment which is described in more detail above.

Drying the treated zirconia article is not absolute necessary, but can be preferred to reduce the time needed for firing and to avoid undesired in-homogenous colour effects. Drying can be effected by simply storing the zirconia article e.g. on a plate at ambient conditions for a couple of hours (about 1 to about 3 h). If, however, a high boiling solvent is used, drying might be difficult to achieve.

According to one embodiment the zirconia ceramic article has the shape of a dental ceramic article.

The dental ceramic article may have the shape of a crown, bridge, inlay, onlay, veneer, facing, coping, crown and bridged framework, implant, abutment, orthodontic appliances (e.g. brackets, buccal tubes, cleats and buttons) and parts thereof and parts thereof.

According to one embodiment, the solution is only applied in the area of the incisal edge of a dental restoration.

According to another embodiment the dental ceramic article may have at least two sections, section A and B, section A having been treated with the solution as described in the present text and section B not having been treated with the solution as described in the present text.

The invention is also directed to the zirconia article obtainable or obtained according to the process described in the present text. Such an article is typically characterized by comprising a section which is more translucent than other sections of the article.

The heat treatment for obtaining the sintered zirconia ceramic article is typically done under the following conditions:
- temperature: from about 900 to about 1500° C. or from about 1000 to about 1400° C. or from about 1100 to about 1350° C. or from about 1200 to about 1400° or from above about 1300 to about 1400° C. or above about 1320° C. to about 1400° C. or above about 1340° C. or above about 1350° C.;
- atmosphere: air or inert gas (e.g. nitrogen, argon);
- pressure: ambient pressure;
- duration: until a density of about 95 to about 100% of the final density of the material has been reached.

The dwell time (that is the time during which the article is kept at that temperature) is not really critical. The dwell time can be zero. The dwell time, however, can also be in a range from about 0 to about 24 h or from about 0.1 to about 5 h.

The invention is also directed to the use of the solution as described in the present text for enhancing the translucency of a zirconia article (e.g. of at least a section thereof) after sintering or alternatively to a process for enhancing the translucency of a zirconia article, the process comprising the steps of applying the solution to at least a part of the zirconia article and sintering the zirconia article.

The solution of the invention does typically not contain components which might produce a toxic, injurious, or immunological response in living tissue or components or additives which jeopardize the intended purpose to be achieved with the present invention, especially in the sintered ceramic.

Thus, for examples components or additives added in an amount which finally (e.g. after a sintering step) results in a non-tooth-coloured article are usually not contained in the final dental restoration. Typically, an article is characterized as tooth coloured if it can be allocated a colour from the Vita™ colour code system, known to the person skilled in the art.

The solution does typically also not comprise insoluble pigments or insoluble additives or thickening agents like silica (e.g. Aerosil) etc.

Moreover, if possible, the solution should not or only contain a small amount of ingredients which can be detrimental to the firing equipment during the sintering process.

According to a further embodiment, the inventive solution does not contain glass or glass/ceramic particles.

The producing of the zirconia material which can be treated with the solution described in the present text does typically also not require the application of a hot isostatic pressing step (HIP).

The complete disclosures of the patents, patent documents, and publications cited herein are incorporated by reference in their entirety as if each were individually incorporated.

The following examples are given to illustrate, but not limit, the scope of this invention.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

Measurements pH-Value

If desired, the measurement of the pH-value can be achieved by means known by the person skilled in art. E.g. an instrument like Metrohm™ 826 or pH indicator paper can be used.

Viscosity

If desired, the measurement of the viscosity can be done as follows: A viscosimeter MCR300 (from Anton Paar Comp.) is used. A portion of the composition is placed between two steel discs with a diameter of 8 mm and a gap of 1 mm at a temperature of 23° C. The gap is filled completely with the composition. Excess composition is removed. The shear rate between the rotating discs d(gamma)/dt is set constantly to 50 s$^{-1}$. The measurement is done 500 s after starting the shearing process of the composition.

Absorption [Nm]

The absorption was measured with a Photospectrometer Color i7 (X-Rite Corp.) with an optical configuration of d/8° using pulsed xenon light source, D65 calibrated illumination, where a spectral range between 360 and 750 nm with 10 nm wavelength interval was recorded. For this measurements transmission mode were used. Color evaluation was configured with 10° observer, inclusion of specular and UV irradiation. A quartz glass cuvette with a chamber thickness of 1 mm was used. The calibration mode of the spectro must include extended measurements for over light and over dark. Therefore, the cuvette was empty.

For coloring measurement, the cuvette was filled with the solution.

The spectrum between 360 nm and 750 nm for transmission of the light beam was recorded. This spectrum was compared to the spectra of deionized water. Compared means "(measured spectra/water spectra)*100. The absorption at a specific wavelength is "100−transmission".

Contrast Ratio Transmission (CR-T)

CR-T value is the transparency using the contrast ratio method.

From the absorption measurement, the CR-T can be determined automatically by the software, using a formula at the ratio of dark backing to light backing measurement. The CR-T value of the measured solution compared to the CR-T of deionized water multiplied with 100 gives the transparency. The higher the CR-T, the higher is the transparency of the solution.

Method for Measuring N2 Sorption Isotherms, BET Surface Area, Pore Volume, Average Connected Pore Diameter The samples were run on either on a QUANTACHROME AUTOSORB-1 BET Analyzer" (Quantachrome Instruments, Boynton Beach, Fla.) or a BELSORP-mini instrument (BEL Japan Inc., Osaka, Japan). The samples were weighed and outgassed at 200° C. for two days then subjected to a N2 sorption process with an appropriate number and distribution of measurement points, e.g. 55 adsorb points and 20 desorb points from a $p/p_0$ range $1\times10^6$ to 1 and back to 0.05 giving full isotherms. The specific surface area S was calculated by the BET method (Details regarding calculation see Autosorb-1 Operating Manual Ver. 1.51 IV. Theory and Discussion, Quantachrome Instruments, Inc.). The total pore volume $V_{liq}$ is derived from the amount of vapor adsorbed at a relative pressure close to unity ($p/p_0$ closest to 1), by assuming that the pores are then filled with liquid adsorbate (Details regarding calculation see Autosorb-1 Operating Manual Ver. 1.51 IV. Theory and Discussion, Quantachrome Instruments, Inc.). The average pore diameter (d) is calculated from the surface area (S) and the total pore volume ($V_{liq}$): $d=4Vliq/S$ Average Grain Size If desired, the average grain size can be determined with the Line Intercept Analysis.

FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Density

If desired, the density of the pre-sintered or sintered material can be measured by an Archimedes technique. The measurements is made on a precision balance (identified as "AE 160" from Mettler Instrument Corp., Hightstown, N.J.) using a density determination kit (identified as "ME 33360" from Mettler Instrument Corp.).

To measure the density of the pre-sintered material the sample is first weighed in air (A). Then the sample is immersed in water using vacuum overnight. The immersed sample is weighed in air (B) and then weighed under water (C). The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho=(A/(B-C))\,\rho0$, where $\rho0$ is the density of water.

To measure the density of the sintered material the sample is first weighed in air (A), then immersed in water (B) The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho=(A/(A-B))\,\rho0$, where $\rho0$ is the density of water.

The relative density can be calculated by reference to the theoretical density ($\rho t$) of the material, $\rho rel=(\rho/\rho t)100$.

Vickers Hardness

If desired, the Vickers hardness can be determined according to ISO 843-4 with the following modifications: The surface of the samples are ground using silicon carbide grinding paper (P400 and P1200). The test forces are adjusted to the hardness level of samples. Used test forces were between 0.2 kg and 2 kg and were applied for 15 s each indentation. A minimum of 10 indentations is measured to determine the average Vickers hardness. The tests can be conducted with a hardness tester Leco M-400-G (Leco Instrumente GmbH).

Biaxial Flexural Strength

If desired, the biaxial flexural strength can be determined according to ISO 6872 (2008) with the following modifications: The sample is sawn into wafers with a thickness of 1 to 2 mm using a dry or wet cut saw The diameter of the samples should be between 12 and 20 mm. Each wafer is centred on a support of three steel balls. The support diameter depends on the sample diameter and should have maximum 14 mm and should be at least 1 mm smaller than the sample diameter. The punch diameter in contact with the wafer is 3.6 mm. The punch is pushed onto the wafer at a rate of 0.1 mm per min. A minimum of 6 samples is measured to determine the average strength. The tests can be conducted in an Instron 5566 universal testing machine (Instron Deutschland GmbH).

Method for Measuring Weight Percent Solids

The weight percent solids were determined by drying a sample weighing 3-6 grams at 120° C. for 30 min. The percent solids can be calculated from the weight of the wet sample (i.e., weight before drying, $weight_{wet}$) and the weight of the dry sample (i.e., weight after drying, $weight_{dry}$) using the following equation: Wt-% solids=100 ($weight_{dry}$)/$weight_{wet}$.

Method for Measuring Oxide Content of a Solid

The oxide content of a sol sample is determined by measuring the percent solids content as described in the "Method for Measuring Weight Percent Solids" then measuring the oxide content of those solids as described in this section.

The oxide content of a solid was measured via thermal gravimetric analysis (obtained under the trade designation "TGA Q500" from TA Instruments, New Castle, Del.). The solids (about 50 mg) were loaded into the TGA and the temperature was taken to 900° C. The oxide content of the solid is equal to the residual weight after heating to 900° C.

Volume Percent Metal Oxide

The volume percent of oxide present in an aerogel or a calcined metal oxide was determined by back-calculation using shrinkage data and assuming that the final sintered body was a 1 cm cube, 100% dense. The total volume of the aerogel or calcined metal oxide is then $(Vt)=[1/(1-S)]^3$, where S is the fractional shrinkage from the aerogel or calcined state to the final sintered material. The volume of metal oxide is the volume of the sintered cube (V)=1. The percent metal oxide (Vol %)=$(1/V_t)100$.

Contrast Ratio Reflectance (CR-R)

CR-R value is the opacity using the contrast ratio method.

CR-R was recorded using a Photospectrometer Color i7 (X-Rite Corp.) with an optical configuration of d/8° using pulsed xenon light source, D65 calibrated illumination, where a spectral range between 360 and 750 nm with 10 nm wavelength interval where recorded. For this measurements reflectance mode with 10 mm aperture where used. Color evaluation was configured with 10° observer, exclusion of specular and inclusion of UV irradiation.

To use this CR-R value, the calibration mode of the spectro must include extended measurements for over light and over dark. Samples must then be measured using both a light backing and a dark backing. The calculation of CR-R is done automatically by the software, using a formula at the ratio of dark backing to light backing measurement.

CR-R is expressed as a percentage. The higher the level of CR-R, the more opaque the material and the lower the level of CR-R, the more translucent the material is.

Materials Used

TABLE 1

| Material name or abbreviation | Description |
|---|---|
| Zirconium acetate | An aqueous solution of zirconium acetate containing nominally 16.3weight percent Zr obtained from Magnesium Elektron, Inc., Flemington, NJ. The aqueous solution was exposed to an ion exchange resin (obtained under the trade designation "AMBERLYTE IR 120" from Rohm and Haas Company, Philadelphia, PA) before use (oxide content 21.85 wt. %) |
| DI water | De-ionized water |
| Yttrium acetate | Yttrium (III) acetate tetrahydrate obtained from AMR Technologies Inc., Toronto, Canada (oxide content 33.4 wt.-%) |
| 2-Hydroxyethyl methacrylate (HEMA) | An acrylate monomer obtained from Aldrich Chemical Company |
| Lanthanum Oxide | Lathanum (III) oxide obtained from Alfa Aesar, Ward Hill, MA (oxide content 99.45 wt. %) |
| 2,2'-Azobis(2-methylbutyronitrile), ("VAZO 67") | 2,2'-Azobis(2-methylbutyronitrile), obtained from E. I. du Pont de Nemours and Company, Wilmington, DE under the trade designation "VAZO 67" |
| Acrylic Acid | Acrylic acid obtained from Alfa Aesar, Ward Hill, MA |
| Ethanol | Ethanol 200 proof obtained from Koptec, King of Prusia, PA |
| Yttrium Carbonate | Yttrium Carbonate hydrate 99.9% from Aldrich |
| Nitric acid | Nitric Acid (65 wt %) from Sigma-Aldrich |
| Chloride acid | Chloride Acid (30 wt %) from Fluka |

Preparation of $ZrO_2$ (88 mol %)/$Y_2O_3$ (12 mol %) Sol (Sol C1)

Sol compositions are reported in mole percent inorganic oxide. Sol C1 was prepared as follows. All other sols were prepared by similar methods in similar equipment.

The hydrothermal reactor was prepared from 15 meters of stainless steel braided smooth tube hose (0.64 cm inside diameter, 0.17 cm thick wall; obtained under the trade designation "DUPONT T62 CHEMFLUOR PTFE" from Saint-Gobain Performance Plastics, Beaverton, Mich.). This tube was immersed in a bath of peanut oil heated to the desired temperature. Following the reactor tube, a coil of an additional 3 meters of stainless steel braided smooth tube hose ("DUPONT T62 CHEMFLUOR PTFE"; 0.64 cm I.D., 0.17 cm thick wall) plus 3 meters of 0.64 cm stainless-steel tubing with a diameter of 0.64 cm and wall thickness of 0.089 cm that was immersed in an ice-water bath to cool the material and a backpressure regulator valve was used to maintain an exit pressure of 2.76 MPa.

A precursor solution was prepared by combining the zirconium acetate solution (2.000 grams) with DI water (2205.3 grams). Yttrium acetate (327.8 grams) was added while mixing until full dissolution. The solids content of the resulting solutions was measured gravimetrically (120° C./hr. forced air oven) to be 22.16 wt.-%. D.I. water (718 grams) was added to adjust the final concentration to 19 wt.-%. This procedure was repeated three times to give a total of about 15.115 grams of precursor material. The resulting solution was pumped at a rate of 11.48 ml/min. through the hydrothermal reactor. The temperature was 225° C. and the average residence time was 42 minutes. A clear and stable zirconia sol was obtained.

Table 2 is a summary of the compositions and the process conditions used for other sols produced in a similar manner to Sol C1.

TABLE 2

| Sol | $ZrO_2$ [mol %] | $Y_2O_3$ [mol %] | $La_2O_3$ [mol %] | Residence time [min] | Temperature, [° C.] |
|---|---|---|---|---|---|
| T1 | 95.7 | 2.3 | 2.0 | 42 | 225 |
| T2 | 97.7 | 2.3 | 0 | 42 | 207 |
| C1 | 88 | 12 | 0 | 42 | 225 |
| C2 | 88 | 12 | 0 | 42 | 207 |

Sol Concentration and Diafiltration

The resulting sols were concentrated (20-35 wt. % solids) first via ultrafiltration using a membrane cartridge (obtained under the trade designation "M21S-100-01P" from Spectrum Laboratories Inc., Rancho Dominguez, Calif.), and then via constant volume diafiltration using the same membrane cartridge. The resulting sol was then further concentrated via rotary evaporation.

Gel Preparation

The gels were prepared by combining the sols to obtain the desired oxide composition and adjusting the oxide, acetic acid and solvent composition via diafiltration, distillation or a combination thereof.

The acrylic acid, hema and initiator were added, the sol placed in a mold and thermally cured at 50 C for 4 hr. A typical procedure is given for G1 below. The composition of the all the gels are given Table 3 (the solvent is made up of water and ethanol).

Example G1

A 141.1 g sample of Sol C1 (prepared and diafiltered and concentrated as described above, 30.4 wt. % oxide and 3.02 wt. % acetic acid) and 400 g of Sol T1 (prepared and diafiltered and concentrated as described above, 44.2 wt. % oxide and 2.30 wt. % acetic acid) were charged in to a 1000 ml RB flask. Water (133.3 g) was removed via rotary evaporation resulting in viscous somewhat dry material. Ethanol (121.2 g), acrylic acid (23.13 g), HEMA (11.8 g) were added to the flask. The contents were stirred overnight resulting is a fluid translucent sol. 2,2'-azobis(2-methylbutyronitrile) ("VAZO 67") (1.2 g) was added and stirred until dissolved. The contents of the flask were then purged with $N_2$ gas for 21 min. The sample (translucent and low viscosity) was charged to cylindrical containers (29 mm diameter). Each container was about 18 ml in volume and each was sealed on both ends (very little air gap was left between the top and liquid). The samples were allowed to stand for about 1 h then placed in an oven to cure (50° C., 4 h). This resulted in a clear translucent blue gel. The gel was removed from the container and placed in a 473 ml wide mouth jar (three gels per jar). The jar was filled with ethanol (275 g, denatured). The sample was soaked for 24 h then the ethanol was replaced with fresh ethanol. The sample was soaked for 24 h then the ethanol was replaced with a third batch of fresh ethanol. The sample was allowed to soak until the supercritical extraction was done. The above manipulations were done minimizing the amount of time the gel was exposed to the air.

Table 3 is a summary of the gel production conditions used for other gels produced in a similar manner to Example G1.

TABLE 3

|  | T-sol:C-sol | T-sol:C-sol (wt. %) | Oxide (wt. %) | Acetic acid (wt. %) | Acrylic acid (wt. %) | Hema (wt. %) | Solvent |
|---|---|---|---|---|---|---|---|
| G-1 | T1:C1 | 75.54:24.45 | 39.33 | 3.34 | 4.14 | 2.13 | 51.06 |
| G-2 | C1:T1 | 75.21:24.79 | 38.9 | 3.75 | 4.14 | 2.12 | 51.09 |
| G-3 | C2:T1 | 75.2:24.7 | 38.9 | 3.81 | 4.14 | 2.13 | 51.02 |
| G-4 | C2:T2 | 50.7:49.3 | 39.7 | 6.1 | 4.24 | 2.17 | 47.79 |

Extraction Process

The gels were loaded into the supercritical extractor. The wet $ZrO_2$-based gels were removed separately from the ethanol bath, weighed, placed individually inside small canvas pouches, and then stored briefly in another ethanol bath before being loaded into the 10-L extractor vessel. The wet weight of some gels of Example G1 was 21.8 grams, 22.7 grams and 22.4 grams. For extraction of the Example G1 gels, about 3500 ml of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. After the extractor vessel lid was sealed in place, liquid carbon dioxide was pumped by a chilled piston pump (setpoint: −12.5° C.) through a heat exchanger to heat the $CO_2$ to 60° C. and into the 10-L extractor vessel until an internal pressure of 11.0 MPa was reached. At these conditions, carbon dioxide is supercritical. Once the extractor operating conditions of 11 MPa and 60° C. were met, a PID-controlled needle valve regulated the pressure inside the extractor vessel by opening and closing to allow the extractor effluent to pass through a porous 316L stainless steel frit (obtained from Mott Corporation as Model #1100S-5.480 DIA-062-10-A), then through a heat exchanger to cool the effluent to 30° C., and finally into a 5-L cyclone separator vessel that was maintained at room temperature and pressure less than 5.5 MPa, where the extracted ethanol and gas-phase $CO_2$ were separated and collected throughout the extraction cycle for recycling and reuse. Supercritical carbon dioxide ($scCO_2$) was pumped continuously through the 10-L extractor vessel for 7 hours from the time the operating conditions were achieved. After the 7-hour extraction cycle, the extractor vessel was slowly vented into the cyclone separator over 16 hours from 11 MPa to atmospheric pressure at 60° C. before the lid was opened and the dried canvas pouches containing the aerogel were removed. The dry Example G1 aerogels were removed from their canvas pouches, weighed, and transferred into 237 ml glass jars packed with tissue paper for storage.

The dry aerogels were semi-translucent with a bluish tint. The dry weights of Example G1 aerogels were 11.9 g, 12.4 g and 12.2 g, corresponding to an overall weight loss during the supercritical extraction process of 45.4%, 45.4% and 45.5%.

Gels from Example G2-G4 were extracted in a similar manner to gels from Example G1.

Burnout/De-Binder Process

The extracted aerogel samples of Example G1 from above were removed from their closed container and set on an aluminium oxide plate, covered with aluminium oxide cylinders and fired in air according to the following schedule in a chamber furnace ("Nabertherm 60 liter"): i—heat from 20° C. to 220° C. at 18° C./h rate; ii—heat from 220° C. to 244° C. at 1° C./h rate; iii—heat from 244° C. to 400° C. at 6° C./h rate; iv—heat from 400° C. to 900° C. at 60° C./h rate; v—hold at 900° C. for 2 h and vi—cool down from 900° C. to 20° C. at 600° C./h rate.

After burnout process, the samples were crack free. The de-bindered samples of Example G1 were sliced into about 2.0 mm thick wafers. Optionally slicing could be done after presintering process. All aerogels from Example G2-G4 were de-bindered in a similar manner to Example G1.

Presintering Process

The de-bindered discs of Example G1 were set on an aluminium oxide plate and fired in air according to the following schedule in a chamber furnace (Nabertherm 1 liter): i—heat from 20° C. to 900° C. at 10° C./min. rate; ii—heat from 900° C. to Tx ° C. at 2° C./min. iii—hold at Tx for y hours and iv—cool down from Tx to 600° C. in 1 h. Pre-sintering steps were finished when furnace was cooled down to room temperature.

Table 4 is a summary of pre-sintering process conditions used for aoregels Example G2-G4, produced in a similar manner as Example G1.

TABLE 4

| Example | Tx [° C.] | y [h] |
|---|---|---|
| G-1A | 1000 | 0 |
| G-1B | 1050 | 2 |
| G-1C | 1050 | 0 |
| G-1D | 1000 | 2 |
| G-1E | 1025 | 2 |
| G-2 | 1020 | 2 |
| G-3 | 1050 | 2 |
| G-4 | 1025 | 2 |

Translucency Enhancing Liquid

For the preparation of the translucency enhancing solution, yttrium carbonate hydrate and nitric acid were used. First, the yttrium oxide content of yttrium carbonate hydrate was determined by thermal gravimetric analysis ("NETZSCH STA 409 C/CD"). In this analysis 70.2 milligrams of yttrium carbonate hydrate were heated from 25° C. with 5° C./min to 1100° C. The weight loss of 42.35% was measured and corresponds to an yttrium oxide ($Y_2O_3$) content of 57.65%.

For Example Y-1, 8 grams of yttrium carbonate hydrate were mixed with 18 ml nitric acid and stirred until the solution was clear. Due to the yttrium carbonate hydrate weight and nitric acid volume, the solution had an yttrium ion concentration of 2.26 mol/l (hydrate and carbonate loss were calculated).

Table 5 is a summary translucency enhancing liquid parameters used for Examples Y2-Y4 produced in a similar manner to Example Y-1.

TABLE 5

| Ex. | Yttrium source | Mass [g] | solvent | Volume [ml] | Concentration [mol/l] |
|---|---|---|---|---|---|
| Y-1 | yttrium carbonate hydrate | 8 | nitric acid | 18 | 2.26 |
| Y-2 | yttrium carbonate hydrate | 10 | nitric acid | 20 | 2.56 |
| Y-3 | yttrium carbonate hydrate | 2.49 | hydrochloridic acid | 50 | 0.25 |
| Y-4 | yttrium carbonate hydrate | 9.79 | hydrochloridic acid | 50 | 1.0 |
| Y-5 | yttrium carbonate hydrate | 7.84 | nitric acid | 20 | 2.0 |

For comparison in Examples VII and VIII commercially available zirconia material was used.

The commercially available Lava™ Plus material (#466760; 3M ESPE) were sliced in discs and soaked with translucency enhancing liquid according the procedure above. The sintering was done according the standard sintering protocol of Lava™ Plus recommended by the manufacturer (3M ESPE).

Results

All samples were polished with a polishing machine (Fa. LECO) using different diamond pastes (e.g. first 20 µm and then 9 µm grain size) to a thickness of 1.00 mm (+/−0.05 mm).

To analyze the translucency enhancing effect, the samples were either observed by human eye and/or the contrast ratio was measured. The results are given in Table 6.

TABLE 6

| Ex. | D | S | YC [mol/l] | ST [min] | SintT [° C.] | TN [mm] | Effect | Before | After | Delta |
|---|---|---|---|---|---|---|---|---|---|---|
| I | G1-A-E | Y-1 | 2.26 | 2 | 1250 | 1.0 | ++ | n.m. | n.m. | n.m. |
| II | G2 | Y-2 | 2.56 | 0.17 | 1250 | 0.85 | ++ | 56.60 | 42.05 | 14.55 |
| III | G3-A | Y-2 | 2.56 | 0.5 | 1250 | 0.9 | ++ | 56.76 | 33.74 | 23.02 |
| IV | G3-B | Y-2 | 2.56 | 2 | 1250 | 0.9 | ++ | 56.76 | 28.84 | 27.92 |
| V | G4-A | Y-3 | 0.25 | 3 | 1325 | 1.0 | − | 56.59 | 55.64 | 0.95 |
| VI | G4-B | Y-4 | 1.0 | 3 | 1325 | 1.0 | + | 56.59 | 44.69 | 10.90 |
| VII | LP | Y-4 | 1.0 | 2 | 1450 | 1.00 | − | 67.06 | 65.26 | 1.8 |
| VIII | LP | Y-5 | 2.0 | 2 | 1450 | 1.00 | − | 67.06 | 64.20 | 2.86 |

D: zirconia disc
S: translucency enhancing solution
YC: concentration of yttrium ions
ST: soak time
SintT: Sintering temperature to full density
TN: Thickness of discs
Effect: Translucency enhancing effect via observation by human eye
Before: contrast ratio reflectance in % without translucency enhancing solution
After: contrast ratio reflectance in % with translucency enhancing solution
Delta: Diffenrence between the contrast ratio reflectance [%] before and after treatment with translucency enhancing solution
"+": indicates significance of effect
"−": no significant effect observed
n.m.: not measured; sample too small; inspected with human eye only
"LP": Lava ™ Plus (3M ESPE)

Soaking/Infiltration Procedure

Pre-sintered discs of Examples G1-A-E were partly or completely soaked for the soaking time of 2 minutes with the translucency enhancing solution of Example Y-1 described above. The samples were dried afterwards on air. Pre-sintered discs of Examples G2-G4 were soaked for a certain soaking time with a translucency limit, both outlined in Table 6.

Sintering

The soaked pre-sintered discs of Examples G1-A-E were fired in air to full density according to the following schedule in a chamber furnace (Nabertherm 1 liter): i—heat from 20° C. to 600° C. at 600° C./h; ii—hold at 600° C. for 1 h; iii—heat from 600° C. to 1000° C. at 600° C./h; iv—heat from 1000° C. to 1250° C. at 120° C./h; v—hold at 1250° C. for 2 h and vi—cool down from 1250° C. to 600° C. in 1 h. Pre-sintered and soaked discs of Examples G2-G4 were sintered to full density in a similar manner to Examples G1-A-E, with minor changes in sintering temperature outlined in Table 6.

In FIG. 1 a picture of the sample obtained according to Example I (G1-C) is shown. The area of the disc treated (soaked, dried and sintered) with the translucency enhancing solution is more translucent than the area not having been treated with the translucency enhancing solution.

Figure 2:
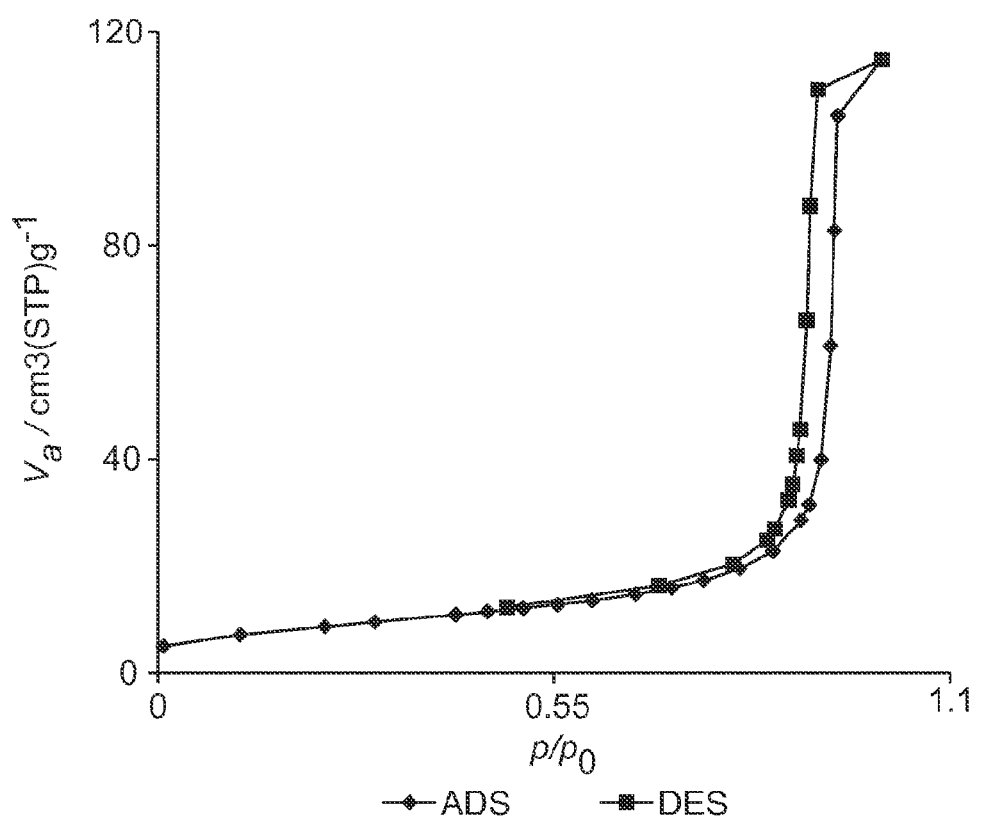
FIG. 2 shows a $N_2$ adsorption and desorption isotherm (sorptions isotherm) obtained when analyzing a sample of the porous zirconia article.

In FIG. 2 a hysteresis loop (type 1 according to IUPC classification) is shown obtained when analyzing a pre-sintered sample produced in accordance to the process described for sample G3 above.

The invention claimed is:
1. Kit of parts comprising:
a solution,
a porous zirconia article,
optionally application equipment,
the solution comprising:
cation(s) of non-colouring agent(s) selected from ions of Y, Gd, La, Yb, Tm, Mg, Ca and mixtures thereof,
solvent(s) for the ion(s),
optionally complexing agent(s),
optionally thickening agent(s),
optionally organic marker substance(s),
optionally additive(s),
the porous zirconia article showing a $N_2$ adsorption and/or desorption of isotherm type IV according to IUPAC classification.

2. The kit of parts according to claim 1, the porous zirconia article being characterized by at least one of the following features:
showing a hysteresis loop when analyzed with regard to the porous zirconia articles nitrogen adsorption and desorption behaviour;
showing a $N_2$ adsorption and desorption isotherm with a hysteresis loop of type H1 according to IUPAC classification;
showing a $N_2$, adsorption and desorption isotherm with a hysteresis loop in a $p/p_0$ range of 0.70 to 0.95;
average connected pore diameter: from 10 nm to 100 nm, from 10 nm to 80 nm or from 10 nm to 50 nm;
average grain size less than 100 nm;
BET surface: from 10 m$^2$/g to 200 m$^2$/g, from 15 m$^2$/g to 100 m$^2$/g or from 16 m$^2$/g to 60 m$^2$/g;
Biaxial flexural strength: from 10 MPa to 40 MPa or from 15 MPa to 30 MPa;
x, y, z dimensions: at least 5 mm, at least 10 mm or at least 20 mm;
Vickers hardness from 25 to 150.

3. The kit of parts according to claim 1, the porous zirconia article being characterized by at least one of the following features:
ZrO2 content from 70 mol % to 98 mol %;
HfO2 content from 0 mol % to 2 mol %;
Y2O3 content from 1 mol % to 15 mol %;
Al2O3 content from about 0 mol % to about 1 mol %.

4. The kit of parts according to claim 1, the porous zirconia article having been obtained by heat treating a zirconia aerogel.

5. The kit according to claim 1, the solution being characterized by at least one of the following features:
the cation(s) of the non-coloring agents) being present in an amount from 0.3 mol to 5 mol per 1 solvent,
the thickening agent(s) being present in an amount from 0 wt.-% to 0.1 wt.-% with respect to the weight of the whole solution,
the complexing agent(s) being present in an amount from 0 mol to 3 mol per 1 solvent,
the organic marker substance(s) being present in an amount from 0 wt. % to 5 wt. % with respect to the weight of the whole solution,
the additive(s) being present in an amount from 0 wt.-% to 5 wt. %,
wt.-% with respect to the weight of the whole composition.

6. The kit according to claim 1, the solution being characterized by at least one of the following features:
the solvent(s) being selected from water, alcohols, ketons and mixtures thereof,
if present, the complexing agent(s) being selected from acetylacetonate, crown ethers, cryptands, ethylenediaminetriacetate and its salts, ethylene diamine tetraacetate and its salts, nitrilotriacetate and its salts, citric acid and its salts, triethylentetramine, porphin, poly acrylate, poly asparagate, acidic peptides, phthalocyanin, salicylate, glycinate, lactate, propylendiamine, ascorbate, oxalic acid and its salts and mixtures thereof;
if present, the thickening agents(s) being selected from polyol(s), glycol ether(s), di- and polyalcohol(s), glycerol ether, polysaccharide(s), xanthan gum, methyl cellulose and mixtures thereof;
if present, the organic marker substance(s) being selected from food colorants and mixtures thereof;
if present, the additive(s) being selected from buffer(s), preservative agent(s), stabilizer(s) and mixtures thereof.

7. The kit according to claim 1, the solution being characterized by at least one of the following features:
having a pH value in the range of 0 to 9;
viscosity: from 1 mPa*s to 10,000 mPa*s;
essentially no light absorption in the range from: 380 nm to 740 nm;
showing a light transmission contrast ratio above 80%;
being non-coloured;
storage stable.

8. The kit according to claim 1, the solution not comprising at least of the following components:
colouring ions selected from ions of Fe, Mn, Er, Pr, V, Cr, Co, Mo and mixtures thereof in an amount above 2 wt.-% with respect to the weight of the solution,
solid particles settling from the solution upon storage for more than 2 hours.

9. The porous zirconia article according to claim 1, the porous zirconia article having a shape of a dental ceramic article.

10. The porous zirconia article of claim 1, the porous zirconia article having a shape of a crown, bridge, inlay, onlay, veneer, facing, coping, crown and bridged framework, implant, abutment, orthodontic appliances and parts thereof and parts thereof.

11. The porous zirconia article of claim 1, the porous zirconia, article having at least two sections A and B, section A having been treated with the solution as described in claim 1, section B not having been treated with the solution as described in claim 1.

12. The porous zirconia article according to claim 1, the zirconia article being characterized by the following features before sintering:
showing a N2 adsorption of isotherm type IV according to IUPAC classification,
showing a N2 adsorption and desorption isotherm with a hysteresis loop of type H1 according to IUPAC classification, especially in a $p/p_0$ range of 0.70 to 0.95,
average connected pore diameter: from 10 nm to 100 nm,
average grain size: less than 100 nm,
BET surface: from 10 m$^2$/g to 200 m$^2$/g or from 15 to 100 m$^2$/g or from 16 m$^2$/g to 60 m$^2$/g,
Biaxial flexural strength: from about 10 MPa to 40 MPa,
x, y, z dimension: at least 5 mm,
Vickers hardness: from 25 to 150,
Density: from 40% to 60% of theoretical density.

13. A method for enhancing the translucency of a zirconia article comprising the steps of
providing a porous zirconia article as described in claim 1 and a solution as described in claim 1,
applying the solution to at least a part of the outer surface of the porous zirconia article,
optionally drying the porous zirconia article of the preceding step,
sintering the porous zirconia article to obtain a zirconia ceramic article.

* * * * *

UNITED STATES PATENT AND TRADEMARK OFFICE
CERTIFICATE OF CORRECTION

PATENT NO. : 9,872,746 B2
APPLICATION NO. : 14/418975
DATED : January 23, 2018
INVENTOR(S) : Holger Hauptmann et al.

It is certified that error appears in the above-identified patent and that said Letters Patent is hereby corrected as shown below:

In the Specification

Column 4
Line 25, delete "ions" and insert -- ions. --, therefor.

Columns 4-5
Lines 66-67 (Column 4), Lines 1-5 (Column 5), delete "The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material)." and insert the same on Column 4, Line 65 as a continuation of the same paragraph.

Column 9
Line 6, delete "mol/l" and insert -- mol/l. --, therefor.

Column 9
Line 11 (approx.), delete "ketons." and insert -- ketones. --, therefor.

Column 9
Line 17 (approx.), delete "aceton" and insert -- acetone --, therefor.

Column 9
Line 58, delete "triethylentetramine," and insert -- triethylenetetramine, --, therefor.

Column 9
Line 60, delete "propylendiamine," and insert -- propylenediamine, --, therefor.

Signed and Sealed this
Fourteenth Day of August, 2018

Andrei Iancu
*Director of the United States Patent and Trademark Office*

Column 10
Line 39, delete "5" and insert -- 5. --, therefor.

Column 11
Line 2, delete "hydrochinone," and insert -- hydroquinone, --, therefor.

Column 11
Line 43, delete "mol/l" and insert -- mol/l, --, therefor.

Column 21
Line 20, delete "16.3weight" and insert -- 16.3 weight --, therefor.

Column 21
Line 24 (approx.), delete ""AMBERLYTE" and insert -- "AMBERLITE --, therefor.

Column 21
Line 31, delete "Lathanum" and insert -- Lanthanum --, therefor.

Column 21
Line 38 (approx.), delete "Prusia," and insert -- Prussia, --, therefor.

Column 22
Line 16 (approx.), delete "$Y_2O_3$" and insert -- $Y_2O_3$ --, therefor.

Column 23
Line 44, delete "DIA-062-" and insert -- DIA-.062- --, therefor.

Column 24
Line 38, delete "aoregels" and insert -- aerogels --, therefor.

Column 25
Line 12 (approx.), delete "hydrochloridic" and insert -- hydrochloric --, therefor.

Column 25
Line 14 (approx.), delete "hydrochloridic" and insert -- hydrochloric --, therefor.

Columns 25-26
Line 38 (approx.), delete "Diffenrence" and insert -- Difference --, therefor.

Column 26
Line 48 (approx.), delete "IUPC" and insert -- IUPAC --, therefor.

In the Claims

Column 27
Line 10, in Claim 2, delete "N₂," and insert -- $N_2$ --, therefor.

Column 27
Line 34, in Claim 5, delete "agents)" and insert -- agent(s) --, therefor.

Column 27
Line 42, in Claim 5, delete "0 wt. %" and insert -- 0 wt.-% --, therefor.

Column 27
Line 42, in Claim 5, delete "5 wt. %" and insert -- 5 wt.-% --, therefor.

Column 27
Line 45, in Claim 5, delete "5 wt. %," and insert -- 5 wt.-%, --, therefor.

Column 27
Line 49, in Claim 6, delete "ketons" and insert -- ketones --, therefor.

Column 27
Line 55, in Claim 6, delete "triethylentetramine," and insert -- triethylenetetramine, --, therefor.

Column 27
Line 57, in Claim 6, delete "propylendiamine," and insert -- propylenediamine, --, therefor.

Column 28
Line 17 (approx.), in Claim 8, delete "at least of" and insert -- at least one of --, therefor.

Column 28
Lines 29-30 (approx.), in Claim 10, delete "and parts thereof and parts thereof." and insert -- and parts thereof. --, therefor.

Column 28
Line 32 (approx.), in Claim 11, delete "zirconia," and insert -- zirconia --, therefor.

Column 28
Line 46 (approx.), in Claim 12, after "15" insert -- $m^2/g$ --.